(12) United States Patent
Cross et al.

(10) Patent No.: US 9,304,091 B2
(45) Date of Patent: Apr. 5, 2016

(54) APPARATUS AND METHOD FOR INSPECTING ARTICLES

(71) Applicant: PCC AIRFOILS, INC., Beachwood, OH (US)

(72) Inventors: Andrew M. Cross, Willoughby, OH (US); Matt Viau, Willoughby, OH (US)

(73) Assignee: PCC AIRFOILS, INC., Beachwood, OH (US)

( * ) Notice: Subject to any disclaimer, the term of this patent is extended or adjusted under 35 U.S.C. 154(b) by 0 days.

(21) Appl. No.: 14/081,498

(22) Filed: Nov. 15, 2013

(65) Prior Publication Data

US 2014/0139827 A1    May 22, 2014

Related U.S. Application Data

(60) Provisional application No. 61/727,303, filed on Nov. 16, 2012.

(51) Int. Cl.
  *G01N 21/00* (2006.01)
  *G01N 21/95* (2006.01)

(52) U.S. Cl.
  CPC .................................. *G01N 21/9515* (2013.01)

(58) Field of Classification Search
  CPC ...... G01B 11/245; G01B 11/02; G01B 11/25; G01B 11/2522; G01B 11/24; G01B 11/2518; G01B 1/00; G01B 21/042; G01J 2005/0077; G01J 5/0014; G01J 5/0088; G01N 21/8806; G01N 2291/2694; G01N 25/72
  See application file for complete search history.

(56) References Cited

U.S. PATENT DOCUMENTS

| | | | |
|---|---|---|---|
| 4,283,835 A | | 8/1981 | Obrochta et al. |
| 4,709,156 A | * | 11/1987 | Murphy et al. .......... 250/559.22 |
| 4,908,782 A | * | 3/1990 | Pekarek et al. ............... 702/167 |
| 5,580,837 A | | 12/1996 | Dodds et al. |
| 5,738,493 A | | 4/1998 | Lee et al. |
| 7,327,857 B2 | * | 2/2008 | Lloyd et al. ................... 382/106 |
| 7,624,787 B2 | | 12/2009 | Lee et al. |
| 7,913,743 B2 | | 3/2011 | Bedzyk |
| 8,171,978 B2 | | 5/2012 | Propheter-Hinkley et al. |
| 2005/0201611 A1 | * | 9/2005 | Lloyd et al. ................... 382/152 |
| 2007/0090310 A1 | * | 4/2007 | Hamilton et al. ........ 250/559.45 |
| 2007/0217672 A1 | * | 9/2007 | Shannon et al. .............. 382/152 |
| 2010/0003619 A1 | * | 1/2010 | Das et al. ...................... 430/290 |

* cited by examiner

*Primary Examiner* — Michael P Stafira
(74) *Attorney, Agent, or Firm* — Tarolli, Sundheim, Covell & Tummino LLP

(57) ABSTRACT

An apparatus for inspecting an article includes a laser assembly which is operable to direct a laser beam against a series of locations disposed along a line which extends across discontinuities in a surface of the article. The position of at least of one location against which the laser beam is directed is detected. The at least one location is spaced from discontinuities in the surface of the article.

9 Claims, 5 Drawing Sheets

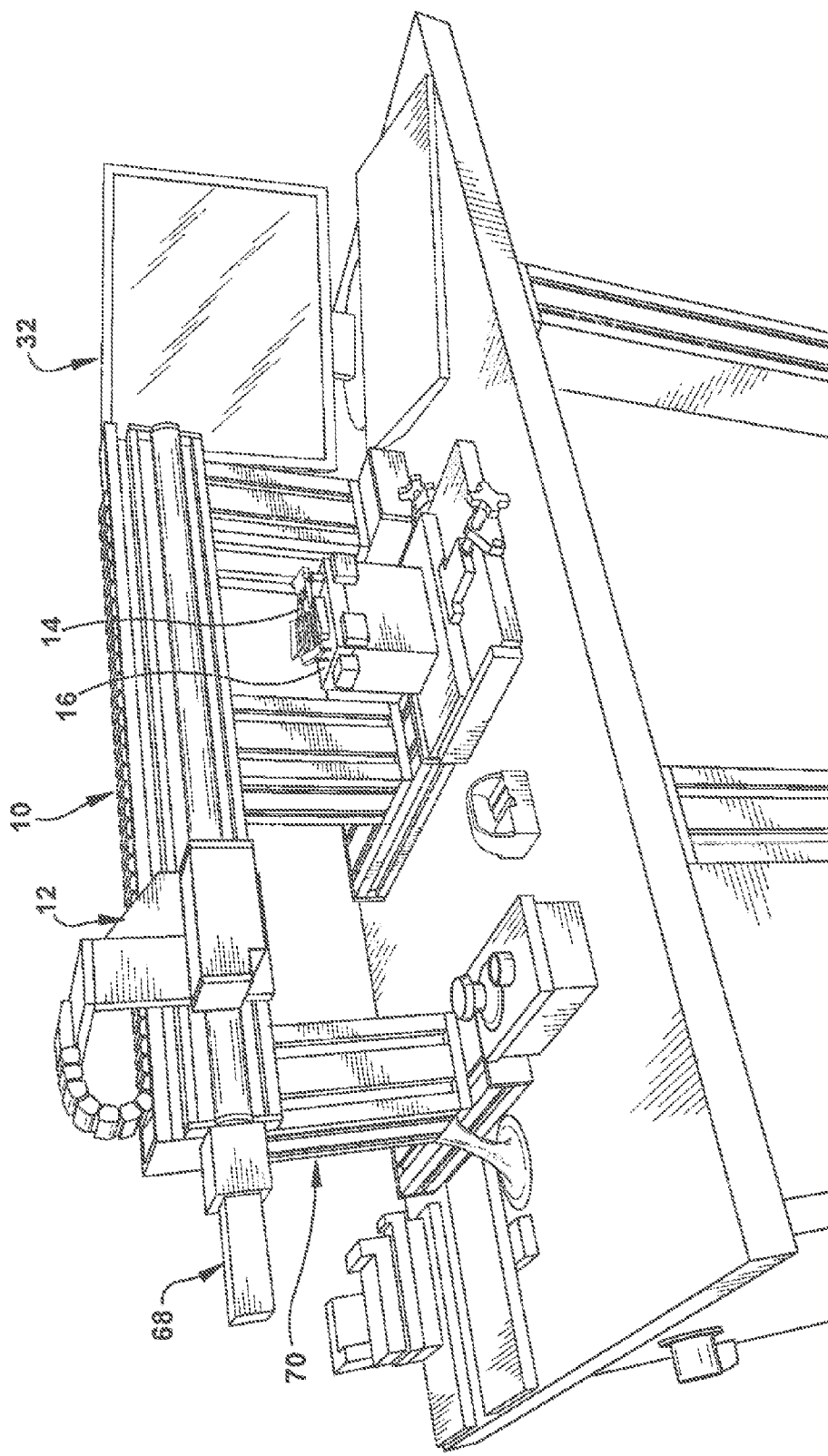

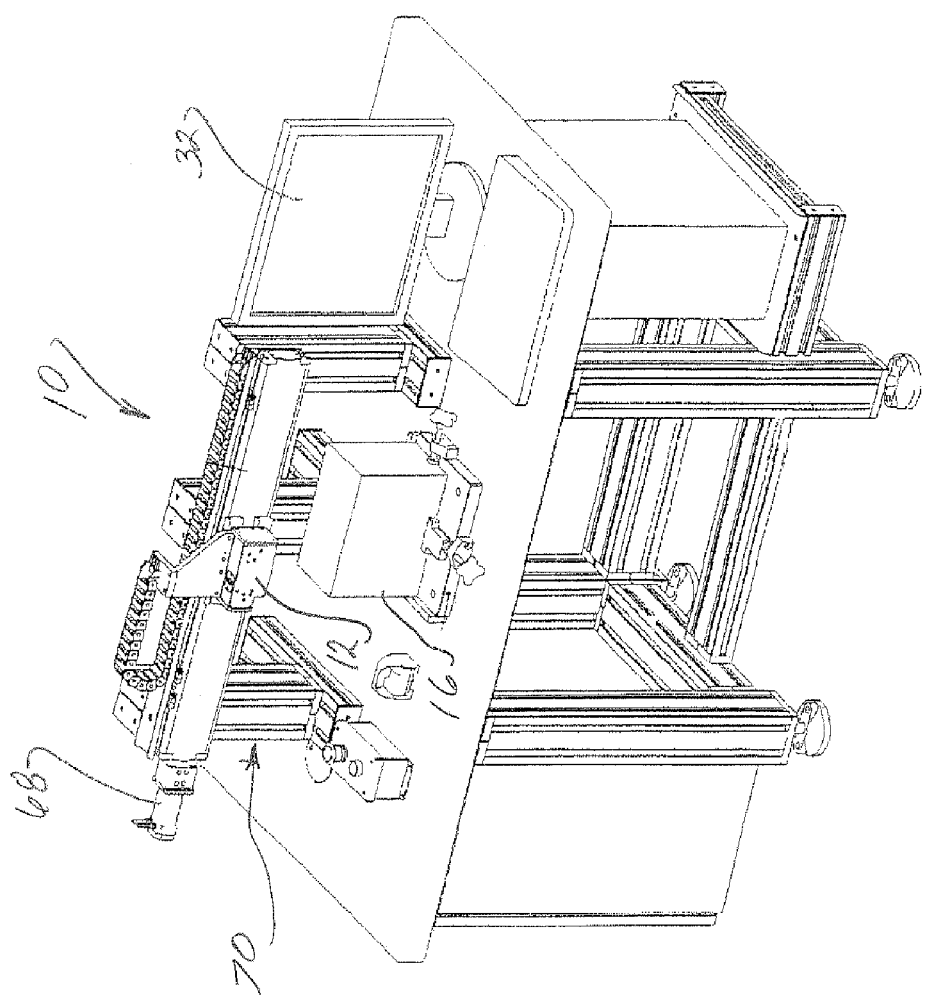

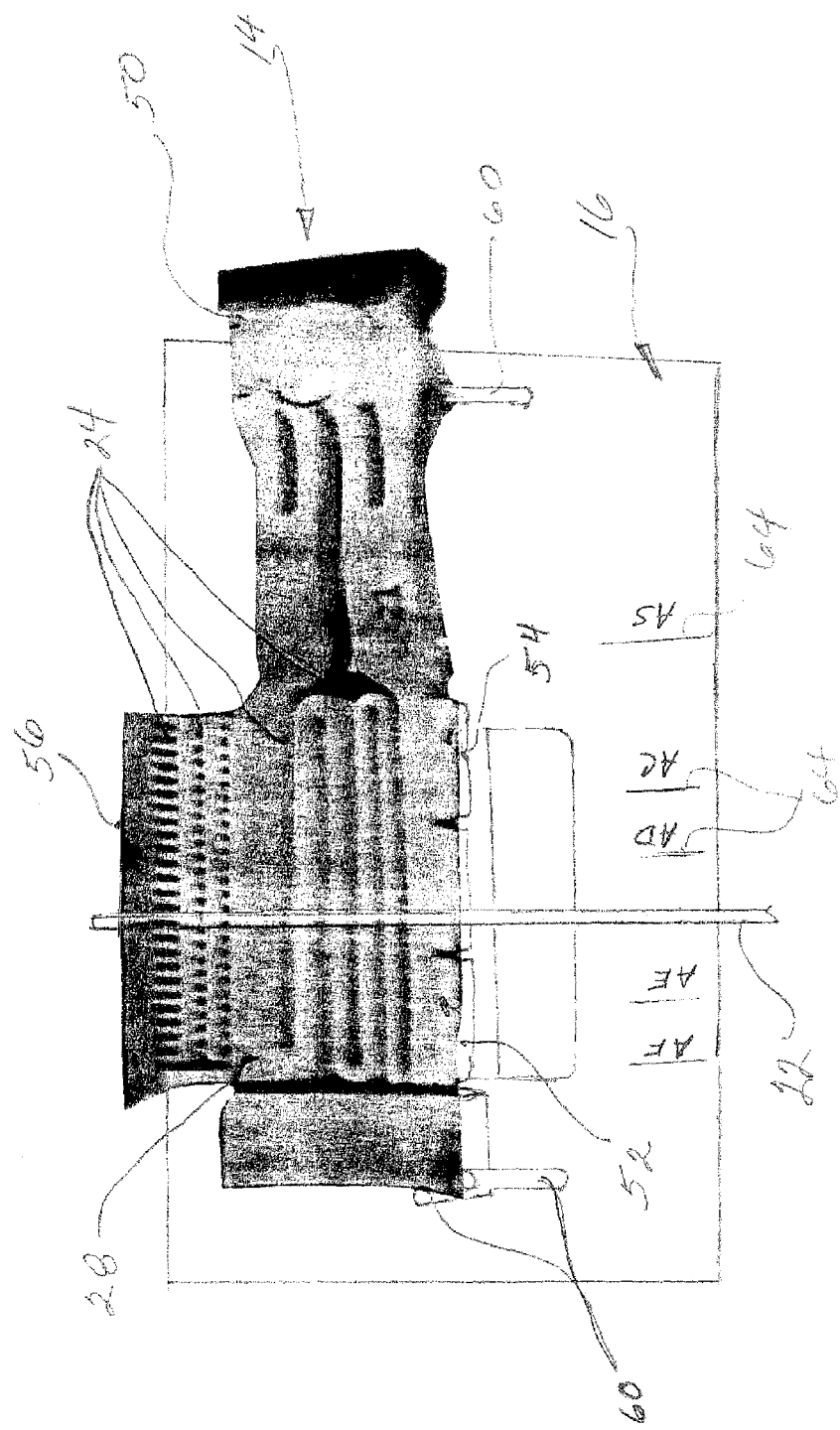

APPARATUS AND METHOD FOR INSPECTING ARTICLES

RELATED APPLICATION

This application discloses subject matter which is disclosed in U.S. Provisional Patent Application Ser. No. 61/727,303 filed Nov. 16, 2012 (Confirmation No. 5225). The disclosure in the aforementioned U.S. Provisional Patent Application Ser. No. 61/727,303 is hereby incorporated herein in its entirety by this reference thereto. The benefit of the earlier filing date of the aforementioned U.S. Provisional Patent Application Ser. No. 61/727,303 is hereby claimed.

BACKGROUND OF THE INVENTION

The present invention relates to a method and apparatus for use in inspecting an article having discontinuities in a surface of the article.

Although the method and apparatus of the present invention may be utilized to inspect many different types of articles. In one specific instance, the method and apparatus are utilized to inspect cores which are utilized to form an interior space in an airfoil. Known cores are illustrated in U.S. Pat. Nos. 5,580,837 and 7,624,787. These known cores and other known cores may be utilized to form a space within an airfoil in the manner disclosed in U.S. Pat. No. 5,738,493.

In the past, cores have been inspected by manually checking cores on a nominal center/form. An individual inspecting the core visually evaluates distortion which appears in a checking section portion of the center/form. This known method involves manual fixing and human interpretation.

Some known cores have had dedicated laser point inspection fixtures which inspect the core displacement at individual points, usually a maximum of five places. These known laser point inspection methods have not provided an inspection of a surface of the core.

Aircraft airfoils cost structure, core type, and volume makes inspecting the cores 100% via coordinate measuring machines or white light non cost effective. Improvements in the design and construction of setter inspections and in relates processes have improved contour inspection capability, but the inherent design and method of using setter blocks can allow unacceptable cores to pass inspection.

SUMMARY OF THE INVENTION

A method and apparatus for use in inspecting an article in which discontinuities are formed includes positioning of the article in a fixture. A laser beam is directed against a series of locations disposed along a line which extends across discontinuities in a surface of the article. The position of at least one location against which the laser beam is directed is detected. The at least one location is spaced from discontinuities in the surface of the article.

It is contemplated that the method and apparatus of the present invention will be utilized to inspect many different types of articles. For example, the apparatus may be utilized to inspect metal or polymeric articles. The method and apparatus may be utilized to inspect ceramic cores which are used to form space within metal airfoils. It is contemplated that the apparatus and method of the present invention will be utilized to inspect many other known articles which are not utilized in turbine engines and/or are not associated with cast metal airfoils.

BRIEF DESCRIPTION OF THE DRAWINGS

The foregoing and other features of the invention will become more apparent upon a consideration of the following description taken in connection with the accompanying drawings in which:

FIG. 1 is an illustration of an apparatus for use in inspecting articles;

FIG. 1A is a simplified schematic illustration further illustrating the apparatus of FIG. 1;

FIG. 2A is a simplified schematic illustration further illustrating the manner in which the laser beam of FIG. 2 is directed against a series of locations disposed along a line which extends across an article being inspected;

DESCRIPTION OF SPECIFIC PREFERRED EMBODIMENTS OF THE INVENTION

An inspection apparatus 10 which is constructed and utilized in accordance with the present invention is illustrated in FIGS. 1 and 1A. The apparatus 10 includes a laser assembly 12 which is utilized to inspect an article 14 disposed on a mounting fixture 16.

Figure 2:
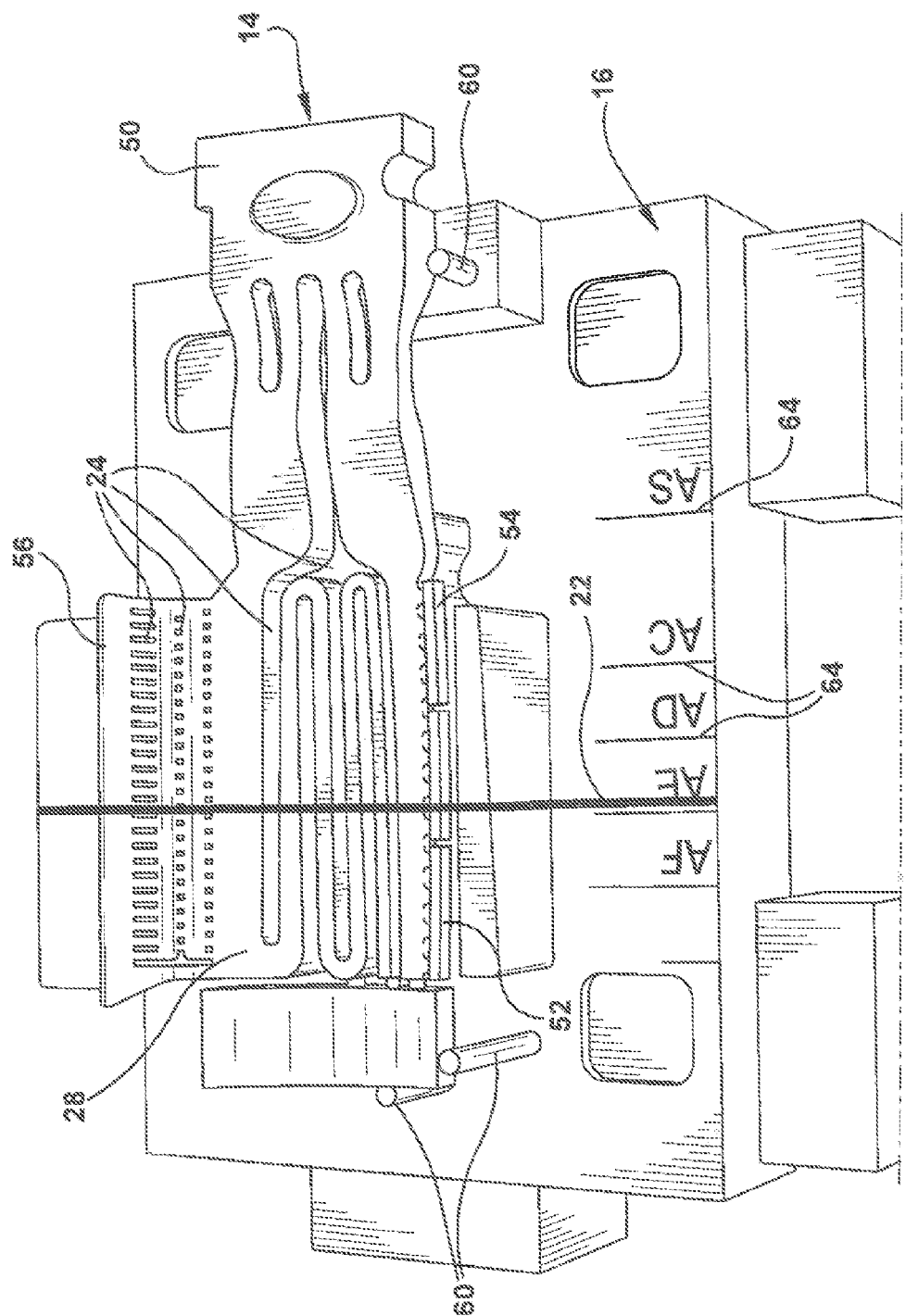
FIG. 2 is a schematic illustration of the manner in which a laser beam is directed against a series of locations disposed along a line which extends across discontinuities in a surface of an article being inspected with the apparatus of FIG. 1.
Figure 3:
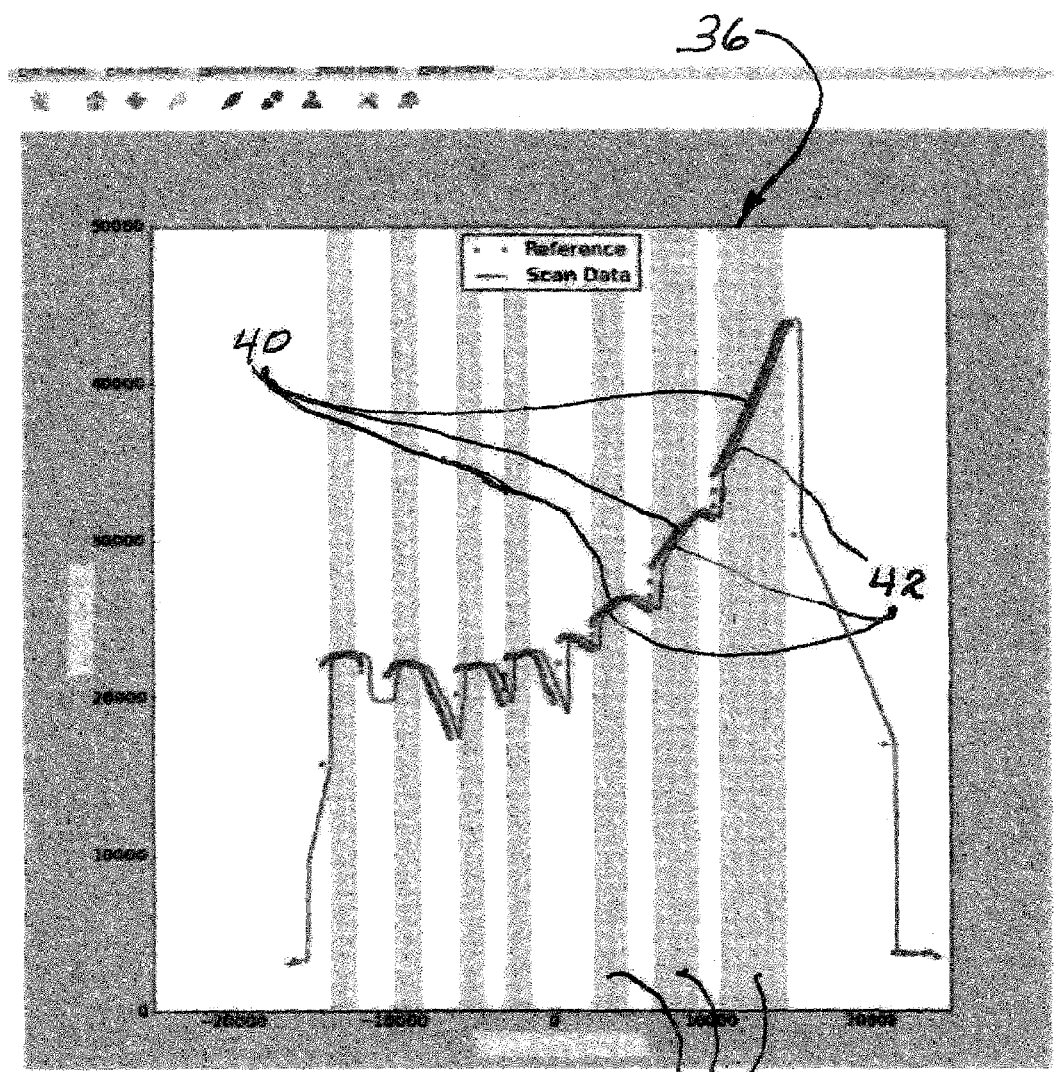
FIG. 3 is a schematic illustration depicting the manner in which data obtained by directing a laser beam against a series of locations disposed along a line which extends across discontinuities in the article of FIG. 2 is compared to reference data at locations spaced from discontinuities in the side surface of the article being inspected.

When the inspection apparatus 10 is utilized to inspect the article 14, a laser beam 22 (FIGS. 2 and 2A) is directed against a series of location disposed along a line which extends across discontinuities 24 in a side surface 28 of the article 14 being inspected. The laser assembly 12 cooperates with a computer 32 (FIGS. 1 and 1A) to provide a read out or graph 36 (FIG. 3). The graph 36 compares reference data, illustrated by lines 40 in the graph 36, with scan data represented by actual surface lines 42. The scan data is obtained from the output of the laser assembly 12 (FIG. 1).

The reference data lines 40 represent a desired configuration for the side surface 28 (FIG. 2) of the article 14 being inspected. The scan data line 42 represents the actual configuration of a surface 28 of the article 14 being inspected. The configuration of the actual surface of the article being inspected is determined by operation of the laser assembly 12. By comparing the actual position of one or more locations along the actual surface line 42 of FIG. 3 to the reference data line 40, it can be determined whether or not the surface of the article 14 is satisfactory.

The laser assembly 12 may have any desired construction. The laser beam 22 may be a series of discreet laser dots or may be a laser stripe. The laser assembly 12 is in active scanner which emits light.

The illustrated laser assembly 12 is a known triangulation laser scanner which shines a laser beam on an object and utilizes a camera to determine the location of a laser dot on the surface 28 of the article 14. The laser beam 22 is formed by a series of laser dots which are spaced one to two thousandths of an inch apart. Whether the laser beam 22 is a series of closely spaced dots or a continuous stripe, the positions of specific locations on the surface 28 of the article 14 against which the laser beam 22 is directed is determined by the laser assembly 12 in cooperation with the computer 32. The locations on the surface 28 of the article 14 which are detected or determined by the laser assembly 12 and computer 32 are at locations which are spaced from the discontinuities 24 in the surface of the article 14.

The discontinuities 24 in the surface of the article 14 may be formed by slots which extend through the article. The discontinuities 24 may be formed by holes or openings which extend through the article 14. The illustrated article 14 has a plurality of slots and a plurality of holes which form the discontinuities 24.

In addition to discontinuities 24 formed by the holes and slots in the article 14, discontinuities are formed in the surface 28 of the article by a series of grooves or recesses in the surface 28 of the article. These recesses do not extend through the article and may be longitudinally extending grooves. Alternatively, the recesses may be cavities which are sunken or depressed below the surface 28 of the article 14 and do not extend through the article. The cavities may be long narrow depressions and/or small pits in the surface 28 of the article 14. Whether the discontinuities extend through the article, as with the holes and slots illustrated in FIG. 2, or extend only partway through the article, it is believed that it will be desirable to determine the position of locations on the surface 28 of the article at locations which are spaced from discontinuities in the surface of the article.

Although it is contemplated that the apparatus 10 may be utilized to inspect many different types of articles, including articles formed of metal and/or polymeric materials, the illustrated article 14 is a ceramic core which is utilized during a lost wax investment casting process to form space within a metal airfoil. The article 14 is a ceramic core having a root end portion 50 and blade portion 52 (FIG. 2). The side surface 28 of the blade portion 52 has a concave configuration and extends between leading and trailing edge portions 54 and 56 of the blade portion 52. The blade portion 52 of the article 14 has a convex side surface opposite from the concave side surface 28. Although the article 14, that is the ceramic core, has been illustrated in FIG. 2 as being oriented in the mounting fixture 16 with the concave side surface facing upwardly, it is contemplated that the article 14 (core) may be positioned in the mounting fixture 16 with the convex side surface facing upwardly.

The mounting fixture 16 (FIG. 2) is a six point nest having a known construction. The mounting fixture 16 may have a construction similar to the construction disclosed in U.S. Pat. No. 7,913,743 if desired. The disclosure in the aforementioned U.S. Pat. No. 7,913,743 is hereby incorporated herein in its entirety by this reference thereto. Alternatively, the mounting fixture 16 may have a construction similar to the construction disclosed in U.S. Pat. No. 4,283,835.

The mounting fixture 16 includes locating pins 60 which engage edge portions of the core 14. In addition, the mounting fixture 16 includes positioning members or pins which engage the convex side of the core 14. It should be understood that any desired number of locating pins or members may be utilized to engage the core 14 at a plurality of locations to properly position the core relative to the mounting fixture 16.

The mounting fixture 16 has reference lines 64 (FIGS. 2 and 2A) which indicate locations where the laser beam 22 is directed onto the upwardly facing side surface of the article (core) 14. In FIG. 2 the reference lines 64 have been designated as AS, AC, AD, AE, and AF. Of course, a greater or lesser number of reference lines 64 may be utilized to indicate locations where the laser beam 22 is to be projected onto the concave upwardly facing side surface 28 of the core 14.

A drive assembly 68 (FIG. 1) is connected with the laser assembly 12. The drive assembly 68 is operable to move the laser assembly 12 along a support structure 70 (FIG. 1) to position the laser beam 22 (FIG. 2) at each of the reference lines 64 in turn. Data resulting from a scanning of the surface 28 of the core 14 with the laser beam 22 is transmitted from the laser assembly 12 to the computer 32 to enable a read out or graph, corresponding to the read out or graph 36 of FIG. 3, to be provided for each of the five locations indicated by the reference lines 64. For each of the scans of the surface 28 of the airfoil 14 by the laser assembly 12, the scan data 42 indicative of the actual position of locations on the surface 28 of the core 14 is compared with data indicative of the desired position of the locations on the surface of the core 14. The manner in which this is done is illustrated by the read out or graph 36 of FIG. 3.

From a comparison of the actual surface data 42 (FIG. 3) to the reference data 40 determined by scanning the surface 28 of the article 14 at each of the reference lines 64, a determination is made by the computer 32 as to whether or not the actual contour of the surface 28 of the core is within an acceptable tolerance range from the desired contour of the surface 28. The data provided by the laser scan enables the actual contour of the surface 28 to be determined at each of the reference lines 64. This enables the actual contour of the surface 28 at each of the reference lines 64 to be compared to the desired contour of the surface 28 at each of the reference lines 64. This enables the determination to be made as to whether or not the contour of the core 14 is within a selected tolerance range relative to the desired contour of the core 14 at each of the reference lines 64.

The positions of actual points on the surface 28, as indicated by the data lines 42, relative to the desired positions of these points, as indicated by the reference data lines 40, is determined between locations where discontinuities 24 are formed in the surface 28. Thus, the positions of a plurality of locations disposed on a surface 28 and spaced from the discontinuities 24 are compared to the positions of a corresponding number of locations on a desired or reference surface. The locations which are spaced from discontinuities in the reference surface are indicated by bands or stripes 66 in FIG. 3.

The locations on the references as desired surfaces to be compared with corresponding locations on the actual surface are disposed within the bands or stripes 66. The bands or stripes intersect the lines 40 indicating the desired or reference surfaces at locations which are free of discontinuities. If the actual surface 28 scanned by the laser beam 22 has the intended configuration, the bands or stripes 66 will intersect the lines 42 indicating the actual surface 28 at locations which are free of discontinuities.

The locations on the actual surface 28 which are compared to locations on a reference surface may be relatively close together, that is, spaced apart by one or two thousandths of an inch. This enables a relatively large number or series of locations disposed on the surface 28 and spaced from the discontinuities 24 to be compared with a large number or series of corresponding reference locations to determine if the configuration of the surface 28 on the core 14 corresponds to a desired configuration for the surface 28. The large number of locations forming a series of locations on the surface 28 of the core 14 are disposed within one of the bands or stripes 66 and are represented by the data 42 in FIG. 3. The reference data 40 is disposed within the same band or stripe 66 as the actual data 42 being compared to the reference data 40.

The comparison of the position of actual locations on the side surface 28 to the positions of corresponding locations on a reference or desired surface enables a determination to be made whether the actual position of a location on the surface 28 is within a selected tolerance range from the position of a corresponding location on a reference surface. The positions of locations on the surface 28 are compared to the positions of corresponding locations on surfaces of a reference at locations which are spaced from the discontinuities 24 in the surface 28.

Having described the invention, the following is claimed:

1. A method of inspecting a ceramic core having an airfoil portion in which discontinuities are formed, said method comprising the steps of positioning the core in a fixture, directing a laser beam against a series of locations disposed along a line which extends across discontinuities in a major side surface of the airfoil portion of the core, and detecting the position of at least one location against which the laser beam is directed, the at least one location being spaced from discontinuities in the major side surface of the airfoil portion of the core.

2. A method as set forth in claim 1 wherein said step of detecting the position of at least one location against which the laser beam is directed includes detecting the positions of a series of adjacent locations against which the laser beam is directed.

3. A method as set forth in claim 1 wherein the discontinuities extend between opposite major side surfaces of the core, said step of directing a laser beam against a series of locations disposed along a line includes directing the laser through at least one of the discontinuities.

4. A method as set forth in claim 1 wherein said step of directing a laser beam against a series of locations disposed along a line which extends across discontinuities in a major side surface of the airfoil portion of the core includes directing the laser beam against a leading edge portion of the airfoil portion of the core and directing the laser beam against a trailing edge portion of the airfoil portion of the core.

5. A method as set forth in claim 1 wherein the airfoil portion of the core has a concave major side surface, said step of directing a laser beam against a series of locations disposed along a line which extends across discontinuities in a major side surface of the airfoil portion of the core includes directing the laser beam against the concave major side surface of the airfoil portion of the core.

6. A method as set forth in claim 1 wherein said step of detecting the position of at least one location against which the laser beam is directed includes detecting the positions of a series of adjacent locations which are disposed on the major side surface of the airfoil portion of the core between first and second adjacent discontinuities in the major side surface of the airfoil portion of the core, comparing data indicative of desired positions of the series of adjacent locations which are disposed on the major side surface of the airfoil portion of the core to data indicative of actual positions of the series of adjacent locations which are disposed on the major side surface of the airfoil portion of the core.

7. A method as set forth in claim 1 further including the steps of determining a plurality of bands which extend across the major side surface of the airfoil portion of the core at locations spaced from discontinuities in the airfoil portion of the core, said step of detecting the position of at least one location against which the laser beam is directed includes detecting actual positions of a plurality of locations disposed along one of the bands, and comparing data indicative of desired positions of the plurality of locations disposed along the one of the bands to the actual positions of the plurality of locations disposed along the one band.

8. A method as set forth in claim 1 wherein said step of detecting the position of at least one location against which the laser beam is directed includes only detecting locations spaced from discontinuities in the major side surface of the airfoil portion of the core.

9. A method as set forth in claim 1 further including directing a laser beam against a series of locations disposed along a plurality of lines which extend across a major side surface of the airfoil portion of the core.

* * * * *